US012059246B2

(12) United States Patent
Orlandi et al.

(10) Patent No.: US 12,059,246 B2
(45) Date of Patent: Aug. 13, 2024

(54) APPARATUS FOR STORING A SAMPLE OF HUMAN BREATH, AND CORRESPONDING METHOD FOR STORING A SAMPLE OF HUMAN BREATH

(71) Applicant: Fondazione IRCCS—Istituto Nazionale dei Tumori, Milan (IT)

(72) Inventors: Rosaria Orlandi, Milan (IT); Pietro Patricola, Milan (IT); Francesco Segrado, Milan (IT); Daniele Veronese, Pogliano Milanese (IT); Paolo Elsi, Pogliano Milanese (IT)

(73) Assignee: Fondazione IRCCS—Istituto Nazionale dei Tumori, Milan (IT)

( * ) Notice: Subject to any disclaimer, the term of this patent is extended or adjusted under 35 U.S.C. 154(b) by 762 days.

(21) Appl. No.: 17/262,258

(22) PCT Filed: Jul. 18, 2019

(86) PCT No.: PCT/IB2019/056152

§ 371 (c)(1),
(2) Date: Jan. 22, 2021

(87) PCT Pub. No.: WO2020/021407

PCT Pub. Date: Jan. 30, 2020

(65) Prior Publication Data

US 2021/0298640 A1 Sep. 30, 2021

(30) Foreign Application Priority Data

Jul. 24, 2018 (IT) ........................ 102018000007477

(51) Int. Cl.

*G01N 33/497* (2006.01)
*A61B 5/097* (2006.01)
*A61B 10/00* (2006.01)

(52) U.S. Cl.

CPC .......... *A61B 5/097* (2013.01); *A61B 10/0096* (2013.01); *G01N 33/497* (2013.01); *A61B 2010/0087* (2013.01)

(58) Field of Classification Search

CPC ............. G01N 33/497; G01N 33/4972; G01N 2033/4975; G01N 2033/4977; A61B 2010/0087; A61B 5/097

See application file for complete search history.

(56) References Cited

U.S. PATENT DOCUMENTS 4,141,354 A * 2/1979 Ismach ............... A61M 16/021 128/204.26
4,332,254 A * 6/1982 Lundquist ........... A61M 25/104 604/920

(Continued)

FOREIGN PATENT DOCUMENTS

DE 4114749 A1 * 11/1991
DE 10059217 A1 * 6/2002 ............ B01L 3/0203

(Continued)

OTHER PUBLICATIONS

International Search Report dated Oct. 25, 2019. 10 pages.

*Primary Examiner* — Herbert K Roberts
(74) *Attorney, Agent, or Firm* — RMCK Law Group PLC

(57) ABSTRACT

Described herein is a method and apparatus for storing a sample of human breath, which includes a metering device having an inlet port and a delivery port; a dispenser device in fluid communication with the delivery port of the metering device; a supply unit configured for delivering a flow of fluid through a delivery port of its own; an acquisition port configured for intake of a sample of human breath; and a selection valve. The selection valve includes a first operating condition, in which a fluid communication is obtained between the acquisition port and the inlet port of the metering device, and a second operating condition, in which (Continued)

a fluid communication is obtained between the delivery port of the supply unit and said metering device.

11 Claims, 6 Drawing Sheets

(56) References Cited

U.S. PATENT DOCUMENTS

| | | | | |
|---|---|---|---|---|
| 5,573,005 | A * | 11/1996 | Ueda | G01N 33/497<br>73/23.3 |
| 2003/0109794 | A1* | 6/2003 | Phillips | G01N 1/2214<br>977/905 |
| 2008/0314452 | A1* | 12/2008 | Smith | G05D 11/006<br>137/101.21 |
| 2010/0049127 | A1* | 2/2010 | Haueter | A61M 5/31525<br>604/246 |
| 2012/0021375 | A1* | 1/2012 | Binner | A61B 5/097<br>433/89 |
| 2015/0335267 | A1* | 11/2015 | Cormier | A61B 5/0836<br>600/532 |
| 2016/0345910 | A1* | 12/2016 | Ahmad | A61B 5/097 |
| 2018/0214050 | A1* | 8/2018 | Purves | G01N 33/004 |
| 2018/0224471 | A1* | 8/2018 | Lynn | G01N 33/948 |

FOREIGN PATENT DOCUMENTS

| | | | | |
|---|---|---|---|---|
| EP | 0338016 | B1 * | 3/1994 | |
| RU | 2265821 | C2 * | 12/2005 | G01N 1/2035 |

* cited by examiner

1
SA
T2
T1
8
20A
20B
6
7
J
19
19B
19A
19D
9
9A
9D
9B
22
21A
21D
21B
21
5P
5D
5
5B
5A
SK
ST
17
13
18
15
14
16
12
3
2
11
10
4

100
T2
SA
T1
8
120
6
7
J
9
9D
9A
9B
119
119B
119A
119D
22
21A
21D
21B
21
3
5P
5D
5
5B
5A
SK
ST
117
113
115
114
112
116
SP
2
11
10
4

1*
SA
T2
T1
8
20B
20A
6
7
J
19
19B
19A
19D
9
9A
9B
9D
21*
5P
5D
5
5B
5A
SK
ST
17
13
18
15
14
16
12
3
2
11
10
4

100*
120
6
7
J
8
T1
T2
SA
119
119B
119A
119D
9
9A
9B
9D
21*
5P
5D
5
5B
5A
SK
ST
117
113
115
114
112
116
SP
3
2
11
10
4

1**
20B
6
20A
SA
T2
T1
8
7
J
19
19B
19A
19D
9**
9A
9D
9B**
22
21A
5P
5D
21D
21B
21
5
5B
17
13
18
15
14
12
16
3
2
11
10
4
5A
ST
SK

APPARATUS FOR STORING A SAMPLE OF HUMAN BREATH, AND CORRESPONDING METHOD FOR STORING A SAMPLE OF HUMAN BREATH

CROSS-REFERENCE TO RELATED APPLICATIONS

This application is a 371 National Stage of International Application No. PCT/IB2019/056152, filed Jul. 18, 2019, which claims priority to Italian Patent Application No. 102018000007477 filed Jul. 24, 2018. The disclosure of each of the above applications is incorporated herein by reference in its entirety.

FIELD OF THE INVENTION

The present invention has been developed with reference to sampling and storage of samples of human breath, in particular for medical analysis.

PRIOR ART

Acquisition of samples of human breath today constitutes a potential instrument for oncological clinical diagnostics in so far as human exhalation may contain various chemical species indicative of onset of pathological cancer conditions. The validity of the analyses of breath lies primarily in the extreme ease that characterises sampling, which is carried out in an altogether non-invasive way and without any particular effort on the part of the patient.

A problem inherent to any sample of human breath is the instability of the sample itself. It is readily subject to contamination, and currently can be stored only in a temporary way in the same container used for sampling, typically a bag made of polymeric material, with one or more taps that enable access to its contents. In fact, it is the sampling container itself that constitutes a potential threat to the integrity of the sample of human breath in so far as the phenomena of dynamic equilibrium that are set up at the interface between the gas exhaled by the patient and the material of the container lead to undesired migration of particles of polymeric material in suspension into the gaseous sample, altering the composition thereof.

To a further reduction of the effectiveness of the sample of human breath there is posed the objective difficulty of long-term conservation thereof. The sampling containers are not able to ensure sealing in regard to exit of gas over a long time, so that it is in effect necessary to carry out the analysis immediately after sampling. In addition to the objective difficulty in handling a large number of samples, the above problem precludes completely the possibility of carrying out further analyses on one and the same sample at separate times.

OBJECT OF THE INVENTION

The object of the present invention is to solve the technical problems mentioned above. In particular, the object of the invention is to enable stable and long-term storage of a sample of human breath, minimising the phenomena of contamination and decay of the sample itself.

SUMMARY OF THE INVENTION

The object of the present invention is achieved by an apparatus and by a method having the features forming the subject of the ensuing claims, which form an integral part of the technical disclosure provided herein in relation to the invention.

BRIEF DESCRIPTION OF THE DRAWINGS

The invention will now be described with reference to the annexed drawings, which are provided purely by way of non-limiting example and in which.

DETAILED DESCRIPTION

Figure 1:
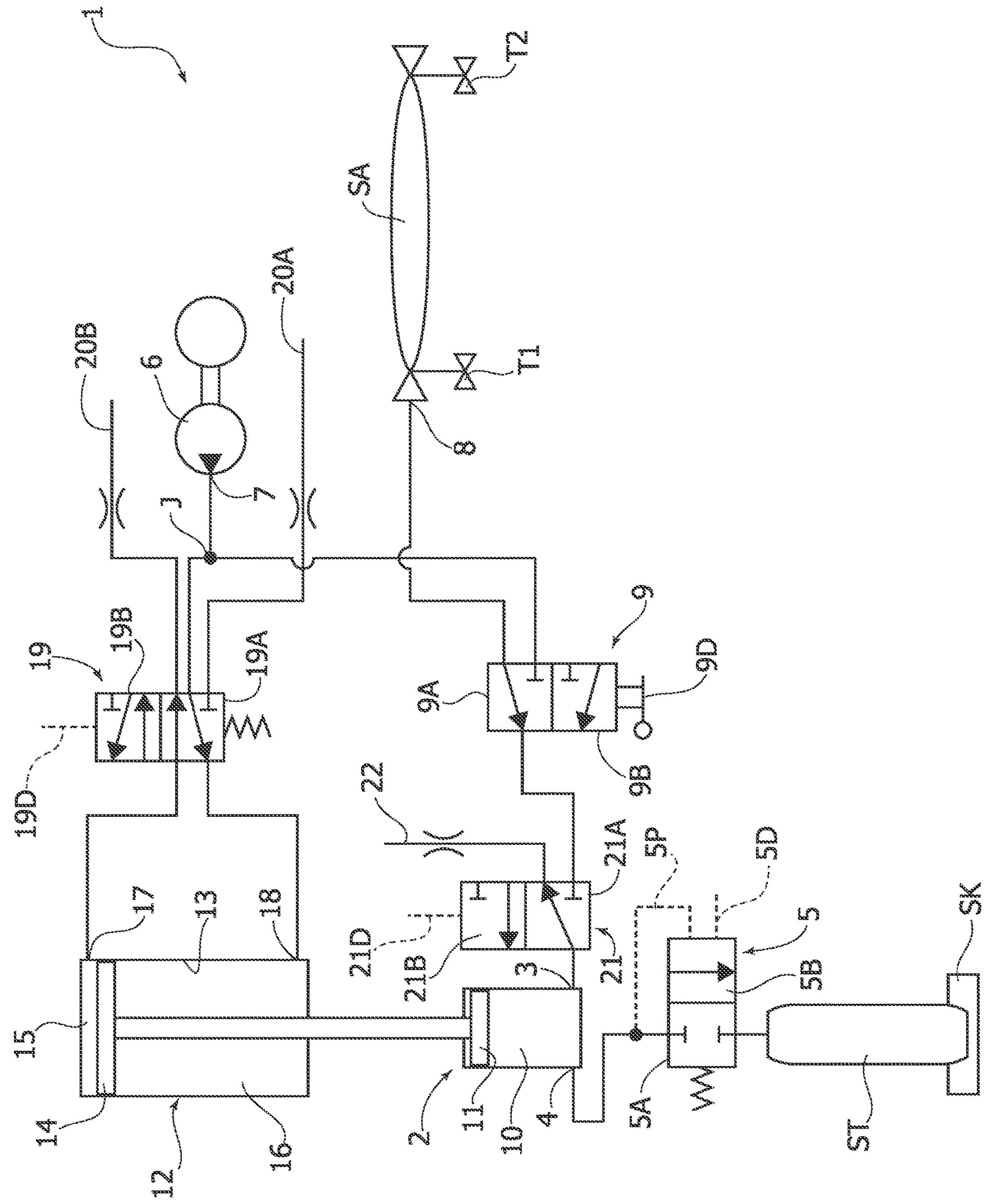
FIG. 1 is a circuit diagram of an apparatus according to the invention.

The reference number 1 in FIG. 1 designates as a whole an apparatus for storing a sample of human breath according to the invention.

The apparatus 1 comprises:

- a metering device 2 having an inlet port 3 and a delivery port 4;
- a dispenser device 5 in fluid communication with the delivery port 4 of the metering device 2;
- a supply unit 6 configured for delivering a flow of fluid through a delivery port 7 thereof;
- preferentially, the supply unit 6 is an active component such as a compressor for air (or gas in general), but in certain variants it is possible to envisage a passive component such as an accumulator of pressurised fluid;
- an acquisition port 8 configured for intake of a sample of human breath; and
- a selection valve 9.

The dispenser device 5 is configured for fluidic connection to a storage container ST, which preferably is an aerosol canister, more preferably an aerosol canister with bag that delimits the active agent (which, in this case, is replaced by the sample of human breath) with respect to the propellant—external to the bag. A housing SK is conveniently provided so as to withhold the container ST firmly coupled to the dispenser device 5.

Figure 2:
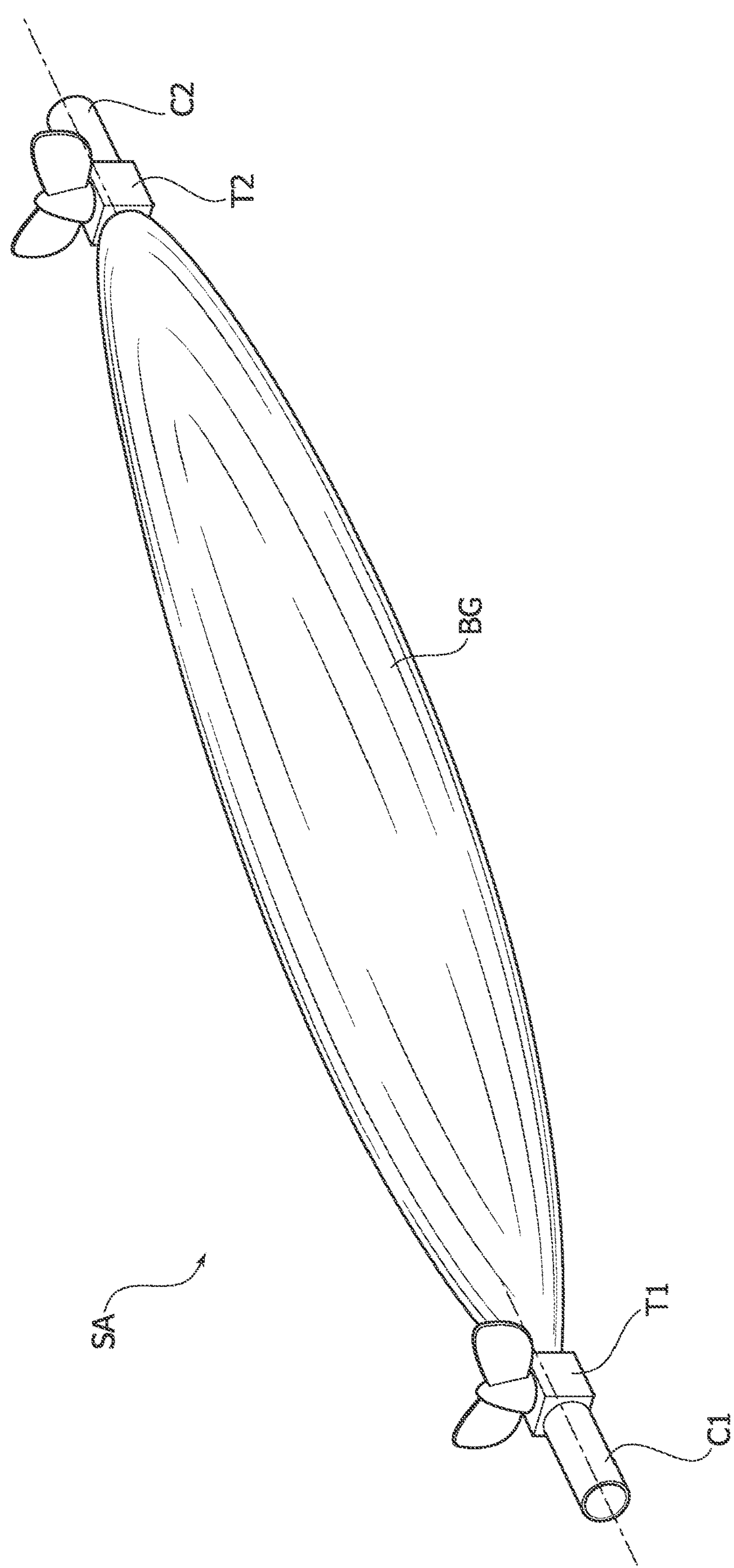
FIG. 2 is a representation provided by way of example of a container for taking a sample of human breath.

The acquisition port 8 is preferably provided as a pneumatic connector, for example a quick-release coupling, to which a container SA for a sample of human breath can be connected. By way of example, the container SA (FIG. 2) includes a bag of polymeric material BG, the ends of which are connected to a first tap T1 and a second tap T2, both equipped with a cannula C1, C2. Each of the cannulas can be used either as mouth-piece for a patient at the moment of exhalation of the sample of breath and as coupling element of a quick-release type that constitutes the port 8.

In other embodiments, the container SA may include just one tap (for example, T1), the other end being blind.

The dispenser device 5 is basically provided as an injection nozzle that can open via mechanical action (in itself known) and is represented schematically in FIG. 1 as a preloaded one-way valve (with two ports and two positions) that can open under pressure and by mechanical action.

The upstream port is connected to the delivery port 4 of the metering device 2, whereas the downstream port is configured for mechanical connection to a loading orifice of the storage container ST.

In a first operating position 5A, the delivery port 4 of the metering device 2 (and the corresponding upstream port to which it is connected) remains isolated, as likewise the downstream port of the dispenser device.

In a second operating position 5B, the delivery port 4 of the metering device 2 (and the corresponding upstream port to which it is connected) is in fluid communication with the downstream port of the dispenser device 5, thus enabling flow from the upstream port to the downstream port.

As represented schematically in FIG. 1, switching from the position 5A to the position 5B may be obtained by fluidic action following upon pressurisation of the circuit stretch comprised between the delivery port 4 and the upstream (this condition being represented schematically by the pilot line 5P) and by mechanical action following upon coupling with the storage container ST (represented schematically by the pilot line 5D). In the latter case, it is the mechanical connection with the container ST that physically defines the pilot mechanism 5D and that physically moves the moving element of the dispenser device 5, bringing it into the position 5B.

The pilot mechanisms 5P and 5D may both be present (as in the diagrams represented in the figures) or else may be present singly, either one or the other, based on how the dispenser device 5 is built. In preferred only the pilot mechanism 5D, or at most a combination of the two pilot mechanisms 5P and 5D. Embodiments in which only the pilot mechanism 5P is present are not preferred—even though they are contemplated by the present invention—primarily in that they can give rise to undesired leak of the sample even when the container ST is not coupled to the dispenser device 5.

The selection valve 9 of FIG. 1 is of the type with three ports and two positions.

The two upstream ports are connected:

i) one to the acquisition port 8; and ii) the other to the delivery port 7 at a circuit node J, while the single downstream port is connected to pneumatic line that proceeds towards the metering device 2.

The valve 9 envisages a first operating condition 9A, in which a fluid communication is obtained between the acquisition port 8 and the downstream port, while the other upstream port (and as a result the delivery port 7) is isolated, and a second operating condition 9B, in which a fluid communication is obtained between the delivery port 7 of the supply unit 6 and the downstream port, while the other upstream port (and as a result the acquisition port 8) remains isolated.

In the preferred embodiment illustrated herein, the metering device 2 is a piston device including a metering chamber 10 into which the inlet port 3 and the delivery port 4 face, and further includes a metering piston 11 movable within the metering chamber 10 between a first operating position and a second operating position (the latter being visible in FIG. 1). The first operating position corresponds to a condition of minimum volume of the metering chamber 10, whereas the second operating condition corresponds to a condition of maximum volume of the metering chamber 10.

Once again with reference to the preferred embodiment represented in FIG. 1, the metering piston 11 is operatively connected for being driven to a linear actuator 12. Preferably, the linear actuator 12 is a double-acting actuator comprising a cylinder 13, mobile in which is a piston 14 that defines a first chamber 15 and a second chamber 16.

Advantageously, the piston 14 has a diameter greater than that of the metering piston 11 so as to obtain in the metering chamber 10 an amplification of the pressure that is exerted on the piston 14. There may, however, be envisaged embodiments that do not follow this criterion, and in particular that envisage identical diameters of the pistons 11 and 14, or else even a diameter of the piston 11 larger than that of the piston 14. The actuator 12 may also be replaced, as will be mentioned hereinafter, by other devices such as an electromechanical linear actuator or a fluid accumulator connected to a chamber of the metering device 2 opposite to the metering chamber 10.

The first chamber 15 and the second chamber 16 each include a respective working port 17, 18 in fluid communication with a distributor valve 19.

The distributor valve 19 is, for example, a distributor with five ports and two positions. The three upstream ports are connected, respectively:

i) to the delivery port 7;

ii) to a first discharge into the atmosphere 20A; and iii) to a second discharge into the atmosphere 20B, while the downstream ports are connected, respectively:

iv) to the chamber 15 of the actuator 12; and v) to the chamber 16 of the actuator 12.

The valve 19 includes a first operating position represented schematically by the block 19A, in which a fluid communication is obtained between the first chamber 15 and the discharge 20B, and between the second chamber 16 and the delivery port 7 of the supply unit 6.

In a second operating position of the distributor valve 19, represented schematically by the block 19B, a fluid communication is instead obtained between the first chamber 15 and the delivery port 7 of the supply unit 6, while the second chamber 16 is connected to the discharge 20A.

Figure 3:
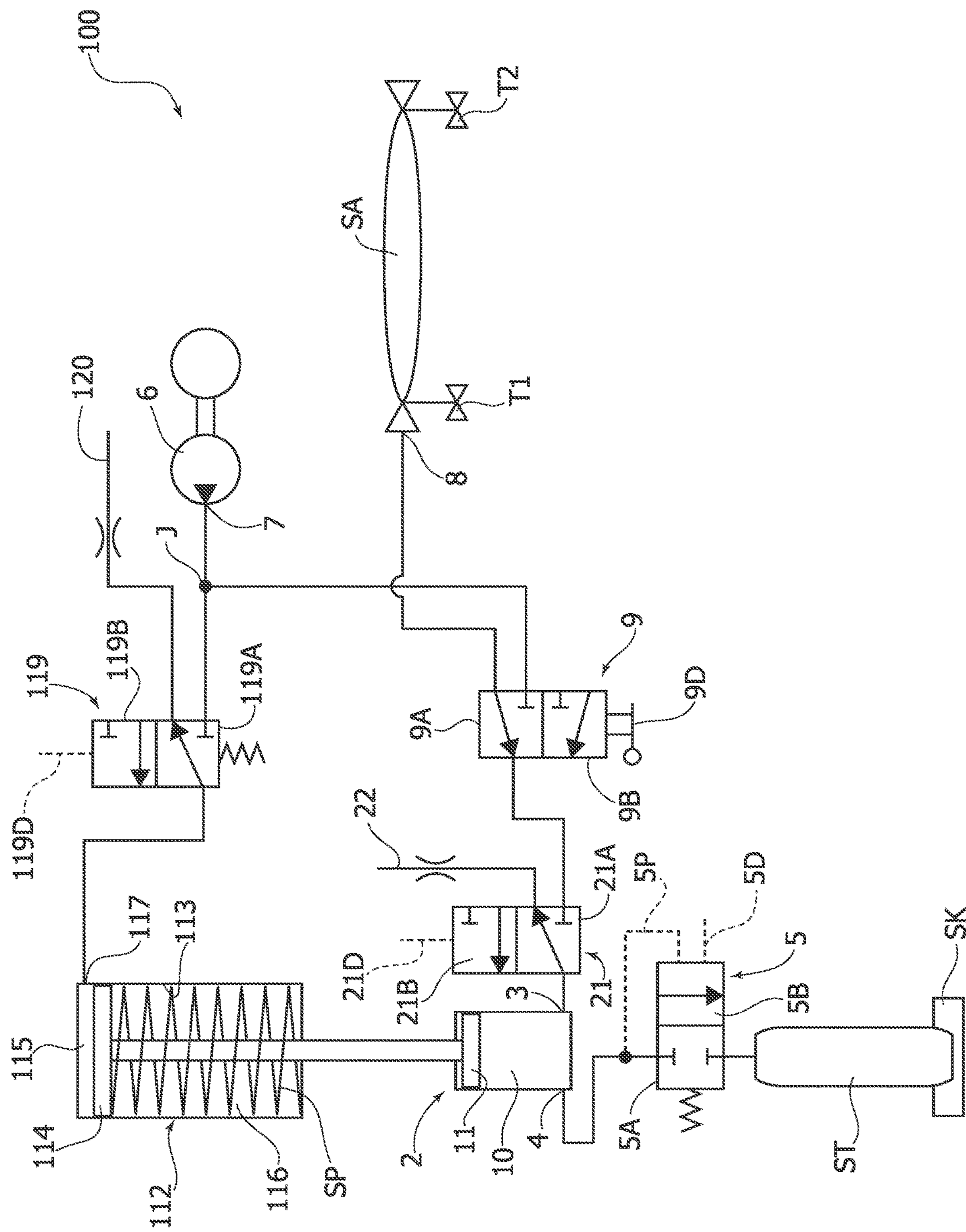
FIG. 3 is a circuit diagram of a second embodiment of the apparatus according to the invention.

In an alternative embodiment represented in FIG. 3 and designated by the reference number 100, the linear actuator 12 is replaced by a single-acting linear actuator 112 comprising a cylinder 113, mobile in which is a piston 114 that delimits—this time only one fluid chamber 115 similar to the chamber 15 of the actuator 12, whereas a volume 116 corresponding to the volume occupied by the chamber 16 in the actuator 12 is occupied by a device for return of the piston, for example a spring SP that is coaxial to the axis of the cylinder or an accumulator of pressurised fluid.

In this embodiment, the distributor valve 19 is replaced by a distributor valve 119 with three ports and two positions 119A, 119B.

The two upstream ports are connected, respectively:

i) to the delivery port 7 at a circuit node J; and ii) to a discharge into the atmosphere 120, while the single downstream port is connected to the chamber 115 of the actuator 112.

In the position 119A (here the resting position), the upstream port connected to the delivery port 7 is isolated, while the single downstream port is connected to the discharge 120. In the position 119B the upstream port connected to the delivery port 7 is connected to the port 117 of the actuator 112, while the upstream port connected to the discharge 120 is isolated.

Whatever the embodiment (1 or 100), set between the valve 9 and the metering device 2 is an exclusion valve 21, here represented schematically as a valve with three ports and two positions. The exclusion valve 21 is configured for selectively isolating supply to the metering chamber 10 of the metering device 2.

The two upstream ports of the exclusion valve 21 are connected, respectively:

i) to a discharge into the atmosphere 22; and ii) to the downstream port of the selection valve 9, while the sole downstream port is connected to the inlet port 3.

In a first operating position, represented schematically by a block 21A, the downstream port (and the chamber 10 therewith) is connected to the discharge into the atmosphere 22 (preferably, it will be provided with a one-way check valve that prevents undesired entry of contaminants from outside) and to the corresponding upstream port, while the second upstream port is isolated, thus cutting off the circuit section upstream thereof from fluid communication with the chamber 10.

In a second operating position (21B), the discharge 22 is isolated (and the corresponding upstream port therewith), while the second upstream port is connected to the downstream port and from here to the inlet port 3.

Figure 4:
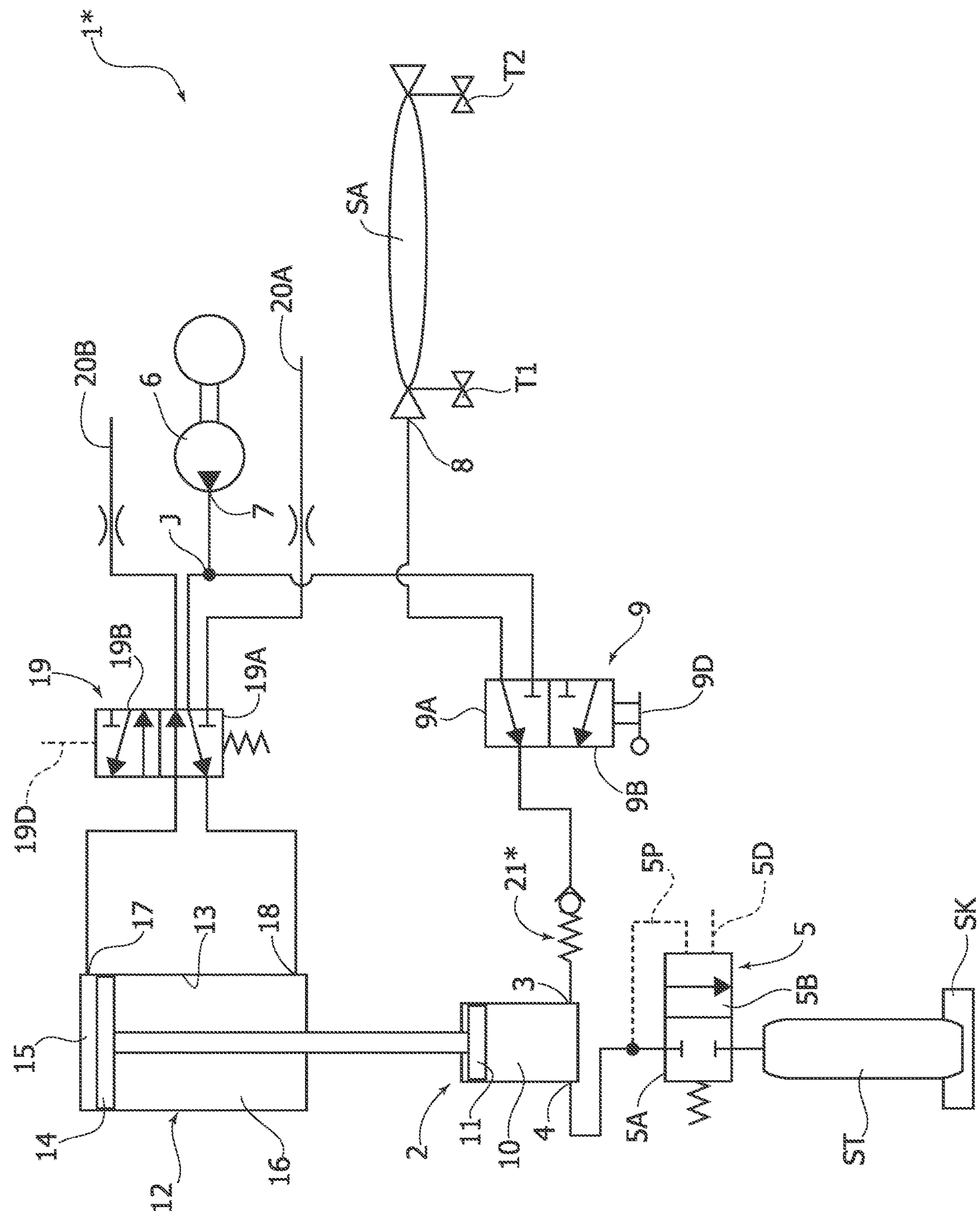
FIGS. 4 and 5 are circuit diagrams of variant embodiments of FIGS. 1 and 3, respectively.
Figure 5:
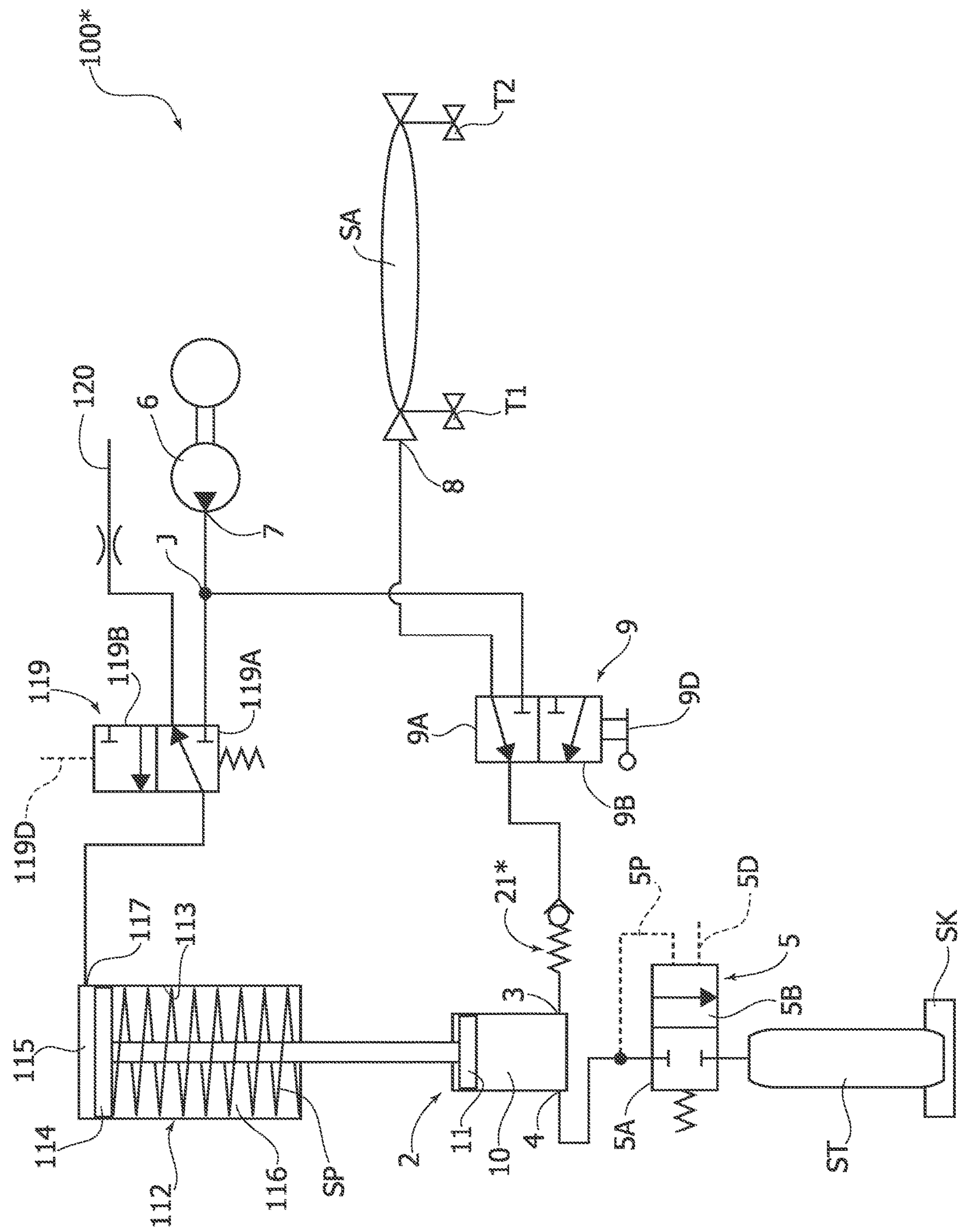

It should, however, be borne in mind, with reference to FIGS. 4 and 5, that, in variants of the apparatuses 1, 100, represented, respectively, in FIGS. 4 and 5, the valve 21 can be replaced by a preloaded one-way valve (which can open under pressure) represented schematically in the aforesaid figures and designated by the reference 21*.

Each of the valves 5 (the dispenser device is at times also referred to as "valve 5"), 9 (selection valve), 19, 119 (distributor valve), 21 (exclusion valve) illustrated herein is associated to a respective pilot mechanism 5D, 9D, 19D, 119D, 21D represented with a dashed line (valves 5, 19, 119, 21) or as manual command (valve 9). This is used to mean, for the purposes of the present description, that the valves in question can be driven either by pneumatic controls or by electrical controls, or again by manual controls according to the needs, or yet again by electromechanical controls that are totally or in part automated. The preferred driving modalities will, however, be described in what follows.

Operation of the apparatuses 1, 1*, 100, 100* is described in what follows. The description will be developed primarily for the apparatuses 1, 1* in so far as operation of the apparatuses 100, 100* is substantially identical, except where otherwise specified.

The apparatus 1 enables intake into the metering chamber 10 of a sample of human breath temporarily stored in the container SA, and subsequently enables loading of the sample itself into the storage container ST for conservation thereof.

From the functional standpoint, the start of a working cycle coincides with the start of the intake stroke of the piston 11; i.e., the metering piston 11 is in the first operating position (minimum volume of the chamber 10), and as a result the piston 14 is in an end-of-travel position at the bottom end of the actuator 12.

From the operative standpoint, this condition may in principle coincide with the condition of end of the previous cycle, but in general depends upon the characteristics of the device dispenser 5. In particular, it may result from a preliminary manoeuvre carried out in the interval between two successive cycles that consists in supply of the chamber 15 by the supply unit 6 with the valve 19 in the position 19B.

In greater detail, in embodiments in which the dispenser device 5 is driven into the open condition by just the pilot mechanism 5D, at the end of a working cycle it is required to bring the piston 11 into the second operating position (maximum volume of the metering chamber 10) to remove the pressure signal 5D, which, when open, enables injection of fluid into the container ST, and thus prevent undesired leaks at the moment of removal of the container ST (i.e., in the lapse of time between detachment of the container ST and mechanical closing of the dispenser 5). This measure is on the other hand even more important in the case where a dispenser device 5 is provided that can open only thanks to the pilot mechanism 5P since in that case there would be produced an uncontrolled expulsion of the sample of breath at the moment of removal of the container ST.

For this reason, at the end of each working cycle the condition is that of a metering chamber 10 at maximum (or practically maximum) volume, with the piston 11 in the second operating position. For the next cycle to start off again, with the piston 11 in the first operating position, i.e., at the start of the stroke for intake of fluid into the chamber 10, it will thus be necessary to carry aforesaid preliminary manoeuvre by supplying the chamber 15 of the actuator 12.

In addition, at initial start-up of the apparatus 1, it is preferable to purge the circuit from possible gaseous residue, so that, assuming that the resting condition for the piston 11 is the second operating position, the preliminary manoeuvre referred to above can be carried out to evacuate the gaseous residue through the dispenser 5 (obviously without any container ST being connected thereto) by bringing the piston 11 back into the first operating position (minimum volume of the chamber 10, start of the intake stroke).

With the above initial conditions, and moreover envisaging:

connection of the container SA, filled with a sample of human breath taken from a patient, to the acquisition port 8;

the valve 9 in the position 9A (in the diagrams of FIGS. 1 and 3, this corresponds to a resting condition, but, in the case where the valve 9 were not already in the resting condition, it would have to be switched into the resting condition);

the distributor valve 19 in the position 19A (as above: in the diagrams this corresponds to the resting condition, but, in the case where the valve 19 were not already in the resting condition, it would have to be switched into the resting condition); and the exclusion valve 21 in the position 21B (in this case, the position 21A is chosen in general as resting position, so that it will be necessary to switch the valve 21 into the position 21B), the tap (T1 or T2) associated to the cannula, by means of which the container SA is connected to the acquisition port 8, is opened.

In the above operating condition, supply of the chamber 16 by the supply unit 6 *a*, with expansion in volume of the chamber 16 and simultaneous reduction in volume of the chamber 15 (the dispenser device 5 is kept in position 5A).

In the case of the apparatus 100, the condition of the valve 9 is unchanged, whereas the valve 119 is in the position 119A (as above, in the diagrams this position corresponds to the resting condition, but in the case where the valve 119 were not already in this position, it would have to be switched into this position) so as to enable the piston 114 to rise by the action of the spring SP.

As a result, the metering piston 11 shifts from the first operating position to the second operating position, drawing into the metering chamber 10 the sample of human breath contained in the container SA.

The apparatus 1, 100 is then ready for loading the sample into the container ST, which is preferably coupled to the dispenser device 5 only at this point (in this way, as anticipated above, the dispenser device 5 is kept closed—position 5A). Coupling of the container ST, in the light of what has been described, enables fluid communication between the delivery port 4 and the loading orifice of the container ST. The valve 19 is switched into the position 19B, enabling supply of the chamber 15 and simultaneous reduction in volume of the metering chamber 10 (with pressurisation of the sample of breath) as a result of shifting of the piston 11 towards the first operating position.

In the case of the apparatus 100, the only difference lies in the fact that it is the valve 119 that is switched into the position 119B, thus supplying the chamber 115 and causing advance of the piston 114 against the action of the spring SP.

The pressurisation undergone by the sample of breath within the metering chamber 10 as a result of the movement of the piston 11 towards the first operating position, allied to the fact that the injection valve 5 switches into the position 5B at the moment of installation of the container ST (and in the embodiments in which opening of the dispenser is obtained by mechanical and pneumatic action—pilot mechanisms 5D+5P—thanks to the fact that the valves 19 and 21 are switched into the respective positions 19B, 21B), results in passage of the sample of breath into the container ST through the valve 5 itself, thus being loaded into the container ST.

Backflow of the sample towards the acquisition port 8 is prevented by a system with a double level of redundancy. In the first place, the valve 9 is built in such a way that in both operating positions 9A and 9B passage of flow of fluid can take place only from the upstream ports to the downstream port, thus preventing backflow on account of the fact that this would have an upstream direction. Moreover, the valve 21 can be switched into the position 21A, thus isolating the metering chamber 10 and discharging into the atmosphere any possible part of the sample that were to be undergo backflow.

The container ST may then be removed from the housing SK and separated from the dispenser device 5. The sample of breath is stored in a safe way and with guaranteed stability even in the long term.

According to an advantageous aspect of the present invention, a specific need that the apparatus 1 must meet is to preventing any cross-contamination of the samples of breath that are loaded in successive cycles. Hence, the fluidic line that comes into contact with the sample of human breath must be scavenged after loading of each sample, for example with inert gas, to prevent the sample loaded from subsequently possibly containing traces of the sample or samples loaded previously. Each cycle of loading of a sample into a container ST terminates with scavenging of the apparatus 1 in the parts that come into contact with the sample of human breath.

To enable scavenging of the fluidic line that comes into contact with the sample of human breath the selection valve 9 is used. In particular, the valve in question is driven into the position 9B, thus setting the delivery port 7 of the supply unit 6 in fluid communication with the inlet port 3 of the metering device 2.

In the embodiments of FIGS. 1 and 3 (apparatuses 1, 100), scavenging also requires the exclusion valve 21 to enable flow towards the chamber 10, which is equivalent to driving the valve into the position 21B. In the variants of FIGS. 4 and 5 (apparatuses 1*, 100*), just the action on the valve 9 is sufficient, since the valve 21* opens automatically under pressure.

An inert gas, for example nitrogen, is then supplied by the supply unit 6 through the valve 9, the valves 21 or 21*, the chamber 10, and the dispenser device 5, through which it evacuates into the atmosphere under mechanical action applied to the dispenser device 5, thus expelling the residue of the previous sample. Advantageously, the same inert gas can be used—as is the case of the apparatus of FIG. 1—also for supply of the actuator 12, so as to simplify the system and reduce the number of components (avoiding, inter alia, the need to provide two supply units).

In the scavenging step, the piston 11 can be kept, once again according to how the dispenser device 5 is built, in the first operating position (scavenging at minimum volume) or in the second operating position (scavenging at maximum volume).

Scavenging at minimum volume is practicable whenever it is not required to remove a pressure signal coming from the chamber 10 (such as the signal 5D) to enable closing of the dispenser device and separation of the storage container ST. Examples thereof are provided by the embodiments of the apparatus 1, 100, 1*, 100*, where the dispenser device 5 is driven only by the mechanical pilot mechanism ST (which is not necessarily limited just to the interaction with the container ST, but is also extended to manual commands independent of the coupling with the container ST). In these embodiments, there is no need to bring the piston 11 back into the second operating position to separate the container ST, so that it can be kept in the first operating position (minimum volume of the chamber 10) for the entire time interval that extends from the end of loading of the container ST to scavenging and connection of a new container SA with a new sample of breath.

This brings with it the advantage of minimising the scavenging volume, albeit cleaning out any possible residue of the sample just loaded from all the parts that come into contact with the sample of human breath.

When for the apparatuses 1, 100, 1*, 100* there is envisaged removal of the pressure signal 5P after loading of the container ST, scavenging is preferably performed with the chamber at maximum volume (piston 11 in the second operating condition). In this case, as already described, an idle stroke of the piston 11 is carried out at the end of loading of the sample into the container ST to bring the piston 11 into the second operating condition, corresponding to the condition of maximum volume of the metering chamber 10, and separate the container ST. In these conditions, scavenging is carried out, it being consequently required to performing a new idle stroke (i.e., the aforesaid preliminary manoeuvre) at the end of scavenging to bring the piston 11 back into the first operating position so that it is ready to carry out a new acquisition of a subsequent sample of human breath.

It should on the other hand be noted that in these embodiments it is in any case possible to carry out scavenging at minimum volume. At the end of the stroke of the piston 11 into the second operating position for detachment of the container ST, the piston 11 itself can be immediately brought back into the first operating position, in part scavenging the chamber 10 by being purged through the dispenser device 5 (and possibly through the discharge 22, keeping the valve 21 in the position 21A). At this point, the valve 9 is switched into the position 9B, and scavenging at minimum volume can then take place as described previously, once again with the advantage of having the piston 11 already in the starting position of the stroke for intake, at the moment of connection, of a new sample of human breath into the sampling container SA.

In brief, via the apparatuses 1, 100, 1*, 100* a method for storing a sample of human breath is hence implemented, which includes:

- providing a container SA filled with a sample of human breath;

connecting the container SA to the acquisition port 8;

controlling a first actuation of the metering device 2 in order to draw the sample of human breath from the container SA, with the selection valve 9 in the first operating condition 9A;

connecting a storage container ST to the dispenser device 5;

controlling a second actuation of the metering device 2 for sending to the dispenser device 5 the sample of human breath drawn in so as to fill the aforesaid storage container ST with the sample;

separating the storage container ST from the dispenser device 5; and bringing the selection valve 9 into the second operating condition 9B and feeding the metering device 2 and the dispenser device 5 with a scavenging fluid (for example, an inert gas) by means of the supply unit 6.

Thanks to the apparatuses 1, 100, 1*, 100* and to the method according to the invention it is thus possible to store stably (and for a long term) a sample of human breath in a pressurised container, for subsequent diagnostic use. Owing to the reduction of the volume of the sample with respect to the volume occupied when it is in the container SA, storage of a large number of samples is facilitated, as is frequently necessary for medical applications. Thanks to scavenging of the circuit carried out at the end of each cycle, each sample is free from cross-contamination by samples processed previously.

Figure 6:
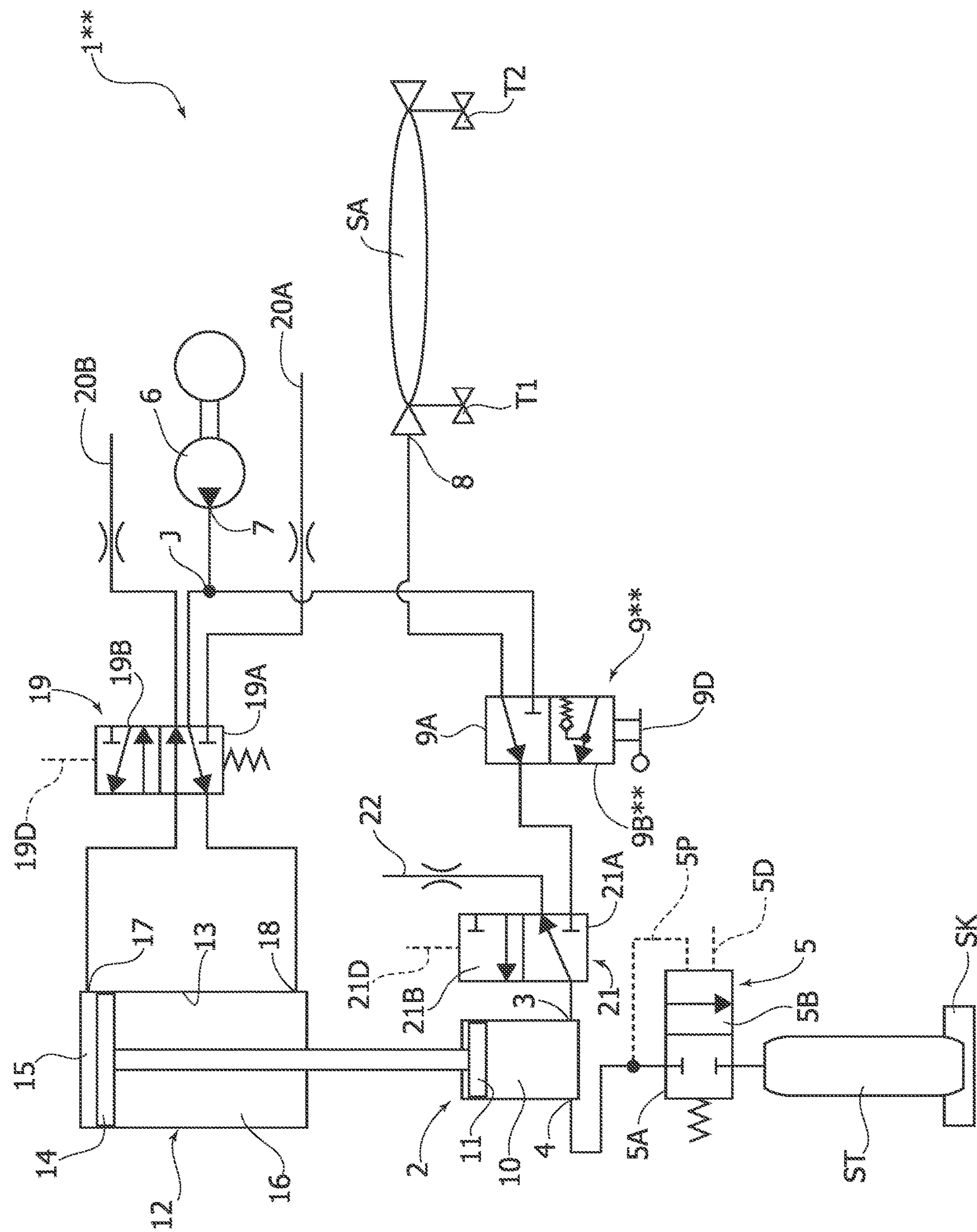
FIG. 6 is a circuit diagram of an apparatus corresponding to that of FIG. 1, but presenting a modification that can be extended to all the embodiments and variants of the invention.

As regards scavenging, FIG. 6 represents a further embodiment of the apparatus 1, designated by the reference 1, which is characterised by a scavenging system with enhanced effectiveness. For economy of description, the modification described herein is only in relation to the apparatus 1**, but may be applied identically to all the apparatuses 100, 1*, 100***.

The apparatus 1 differs from the apparatus 1 only as regards the configuration of the selection valve 9, and in particular as regards the configuration of the second operating condition. The selection valve is here denoted by the reference 9**, while the second operating condition is denoted by 9B. In this operating condition, instead of complete exclusion of the circuit branch that comes under the acquisition port 8, as occurs in the case of the valve 9, the valve 9 in the position 9B provides a fluidic connection—which can open under pressure—between the single downstream port and the upstream port that is connected to the acquisition port 8 (as a result, the pressure-openable connection regards the delivery port 7 of the supply unit and the acquisition port 8).

In this way, at the moment when the pressurised fluid flows into the circuit branch that had previously come into contact with the sample of human breath, a part of pressurised flow opens the fluidic connection (represented schematically by a pressure-openable one-way valve) between the delivery port 7 and the acquisition port 8, thus scavenging the circuit stretch comprised between the valve 9 and the port 8. This embodiment of the selection valve is preferable in particular in the case where—for costructional requirements—there is an appreciable distance between the port 8 and the selection valve such that, upon removal of the container SA, it is difficult to obtain spontaneous scavenging of the stretch in question (a fact, instead, that is practically certain in the case of a very short fluidic stretch between the port 8 and the selection valve). It should, moreover, be borne in mind that the apparatus 1** is here illustrated as being equipped with the valves 21 and 19, but it may alternatively be equipped with the valve 21* and/or the valve 119 (in this case, with the actuator 12 replaced by the actuator 112**).

Of course, the details of construction and the embodiments may vary widely with respect to what has been described and illustrated herein, without thereby departing from the sphere of protection of the present invention, as defined by the annexed claims.

For instance, the linear actuator 12, which is of a pneumatic type, may be replaced, in some embodiments, by an electromechanical actuator, for example a linear wormscrew actuator that acts directly on the metering piston 11, or else an electrically driven toggle mechanism that acts once again on the metering piston 11. This makes it possible to obtain a more compact apparatus by reducing the encumbrance due to the actuator 12.

The invention claimed is:

1. An apparatus for storing a sample of human breath, comprising:

a metering device having a metering member, an inlet port and a delivery port;

a dispenser device in fluid communication with the delivery port of the metering device;

a selection valve;

a supply unit configured for delivering a pressurized flow of fluid through a delivery port thereof, the supply unit delivery port in fluid communication with the selection valve and the inlet port of the metering device; and an acquisition port configured for intake of the sample of human breath, the acquisition port in fluid communication with the selection valve;

wherein said selection valve includes a first operating condition, in which a fluid communication is obtained between the acquisition port and the inlet port of the metering device and the pressurized flow of fluid from the supply unit is configured to move the metering member along an intake stroke and/or an exhaust stroke, and a second operating condition, in which a fluid communication between the delivery port of the supply unit and said metering device is provided to provide scavenging of i) the metering device, and ii) the dispenser device by way of the delivery port of the metering device, using the pressurized flow of fluid from the supply unit.

2. The apparatus according to claim 1, wherein said metering device is a piston device including a metering chamber, opening into which are the inlet port and the delivery port, and the metering member is a metering piston movable within the metering chamber between a first operating position and a second operating position.

3. The apparatus according to claim 2, wherein a displacement of said metering piston from said first operating position to said second operating position provides the intake, into said metering chamber, of the sample of human breath leading to said acquisition port, while a displacement of said metering piston from said second operating position to said first operating position provides delivery to said dispenser device of the sample of human breath taken into the metering chamber.

4. The apparatus according to claim 3, wherein during the displacement of the metering piston from said first operating position to the second operating position for the intake of the sample of human breath into said metering chamber, the selection valve is in the first operating condition.

5. The apparatus according to claim 2, wherein, when the selection valve is in the second operating condition, it is configured to enable a scavenging of said metering chamber and of said dispenser device.

6. The apparatus according to claim 2, further comprising a distribution valve in fluid communication with the supply unit and a linear actuator configured to drive the metering piston between the first operating position and the second operating position, wherein the distribution valve includes:

a first operating position in which fluid communication is established between a first chamber of the linear actuator and a discharge to atmosphere and between a second chamber or the linear actuator and the delivery port of the supply unit; and a second operating position in which fluid communication is established between the first chamber and the deliver port and communication is established between the second chamber and the atmosphere.

7. The apparatus according to claim 2, wherein the metering piston is operatively connected for operation thereof to a linear actuator, said linear actuator being operatively connected to said supply unit by means of a distributor valve.

8. The apparatus according to claim 7, wherein the linear actuator is a double-acting actuator comprising a cylinder, into which a piston is movable that defines a first chamber and a second chamber, wherein each of said first chamber and second chamber includes a respective working port in fluid communication with said distributor valve, wherein the distributor valve includes a first operating mode wherein a fluid communication is provided between said second chamber and the delivery port of the supply unit, while said first chamber is connected to a discharge, and a second operating mode, in which a fluid communication is provided between said first chamber and the delivery port of the supply unit, while said second chamber is connected to a discharge.

9. A method for storing a sample of human breath by means of an apparatus according to claim 7, the method including:

providing a sampling container filled with the sample of human breath;

connecting the sampling container to the acquisition port;

controlling a first actuation of the metering device to draw the sample of human breath from said sampling container, the selection valve being in the first operating condition;

connecting a storage container to said dispenser device;

controlling a second actuation of the metering device to deliver the sample of human breath drawn into the dispenser device, so as to fill said storage container with the sample of human breath;

separating the storage container from said dispenser device; and bringing the selection valve into the second operating condition and feeding the metering device and the dispenser device with a scavenging fluid by means of the supply unit.

10. The method according to claim 9, wherein said controlling a second actuation of the metering device is carried out by sending a flow of said scavenging fluid to said linear actuator by means of said supply unit.

11. An apparatus for storing a sample of human breath, comprising:

a metering device having an inlet port and a delivery port;

a dispenser device in fluid communication with the delivery port of the metering device;

a supply unit configured for delivering a flow of fluid through a delivery port thereof;

an acquisition port configured for intake of the sample of human breath; and a selection valve, wherein said selection valve includes a first operating condition, in which a fluid communication is obtained between the acquisition port and the inlet port of the metering device, and a second operating condition, in which a fluid communication between the delivery port of the supply unit and said metering device is provided, wherein in the second operating condition of the selection valve, there is provided a fluidic connection that is configured to be opened under pressure between the delivery port of the supply unit and said acquisition port.

* * * * *